United States Patent
Matsumori

(10) Patent No.: US 6,214,535 B1
(45) Date of Patent: *Apr. 10, 2001

(54) METHOD FOR TESTING CARDIAC MYOCARDITIS OR CARDIOMYOPATHY

(75) Inventor: Akira Matsumori, Osaka (JP)

(73) Assignee: Toray Industries, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,620

(22) PCT Filed: Aug. 30, 1996

(86) PCT No.: PCT/JP96/02437

§ 371 Date: Apr. 16, 1997

§ 102(e) Date: Apr. 16, 1997

(87) PCT Pub. No.: WO97/07820

PCT Pub. Date: Mar. 6, 1997

(30) Foreign Application Priority Data

Aug. 30, 1995 (JP) .................................................. 7-222224

(51) Int. Cl.⁷ ........................................................ A01N 1/02
(52) U.S. Cl. ........................... 435/2; 514/2; 435/5; 435/6
(58) Field of Search ................................. 514/2; 435/5, 6

(56) References Cited

U.S. PATENT DOCUMENTS

| | | | |
|---|---|---|---|
| 4,041,152 | * | 8/1977 | Chany ..................................... 424/85 |
| 4,216,203 | * | 8/1980 | Johnston ................................ 424/85 |
| 4,241,174 | * | 12/1980 | Familletti ................................ 435/5 |
| 4,257,938 | * | 3/1981 | Hosoi ................................. 260/112 R |
| 5,372,808 | * | 12/1994 | Blatt ..................................... 424/85.4 |
| 5,464,020 | * | 11/1995 | Lerner ................................... 128/696 |
| 5,622,848 | * | 4/1997 | Morrow ............................. 435/173.1 |
| 5,643,564 | * | 7/1997 | Hamaguchi .......................... 424/85.1 |
| 5,695,766 | * | 12/1997 | Paul ................................... 424/204.1 |

FOREIGN PATENT DOCUMENTS

WO 88 03411   5/1988   (WO) .

OTHER PUBLICATIONS

Schlauder et al., Detection of hepatitis C viral RNA by the polymerase chain reaction in serum of patients with post–transfusion non–A, non–B hepatitis. J. Virol. Methods 37:189–200, 1992.*

Lim et al., Cholestatic Hepatitis Leading to Hepatic Failure in a Patient With Organ–Transmitted Hepatitis C Virus Infection. Gastroenterology 106:248–251, 1994.*

Matsumori, J. Am. Coll. Cardiol. 9, 1320–25, No Year 1987.*

Matsumori, Japanese Circulation Journal 51, 1362–64 No Year 1987.*

Matsumori, Japanese Circulation Journal 51, 661–64 No Year 1987.*

Matsumori, A., et al., "Detection of hepatitis C virus RNA from the heart of patients with hypertrophic cardiomyopathy" Biochemical and Biophysical Research Communications, vol. 222, No. 3, May 23, 1996, pp. 678–682.

Matsumori, A., et al., "Dilated Cardiomyopathy Associated With Hepatitis C Virus Infection," Circulation, vol. 92, No. 9, pp. 2519–2525, 1995.

* cited by examiner

*Primary Examiner*—Donna Wortman
(74) *Attorney, Agent, or Firm*—Fish & Richardson P.C.

(57) ABSTRACT

The present invention relates to a method for the treatment of cardiac disease resulting from a viral infection of the cardiac tissue with human hepatitis C virus or EMC virus comprising administering an antiviral agent to a subject. The antiviral agent is useful in the treatment of myocarditis and cardiomyopathy.

3 Claims, No Drawings

METHOD FOR TESTING CARDIAC MYOCARDITIS OR CARDIOMYOPATHY

TECHNICAL FIELD

The present invention relates to a therapeutic agent for a cardiac disease in which the cardiac muscle tissue is infected with human hepatitis C virus and a method for testing a cardiac disease.

BACKGROUND ART

Myocarditis is a disease caused by infection, allergy, poisoning or the like which will lead to inflammatory myocardial disorders and most of myocarditis is believed to be viral. As causative viruses, a number of enteroviruses are considered. In particular, Coxsackie B virus is believed to cause viral myocarditis most frequently. However, as viruses associated with cardiac diseases, various viruses such as influenza virus, Coxsackie A virus, cytomegalovirus, parainfluenza virus are reported in addition to Coxsackie B virus, and the major causative virus has not been ascertained yet (Akira Matsumori, *Circular System Now No. 6: Cardiomyopathy/Myocarditis*, Nanko-Do Co., p. 36, 1994).

The search for a causative virus has been performed mainly by an indirect method in which a virus antibody is detected in a serum. There has been almost no direct proof from the cardiac muscle. One of the reasons for this is that, since a virus which has invaded the cardiac muscle disappears in several days, it is almost impossible to identify a causative virus in the cardiac muscle, particularly in a clinical scene.

Recently, by the application of dot blotting, slot blotting and nucleic acid hybridization techniques such as in situ hybridization, a study using a cardiac muscle biopsy specimen has become possible. As a result, it has been shown that viral genes remain in tissues for a longer period than expected, and the possibility of viral continuous infection has been suggested. Also, by the recently developed polymerase chain reaction (PCR) method, it has become possible to detect with a higher sensitivity viral genome in cardiac muscle biopsy and autopsy specimens.

However, even with these genetic analysis techniques, results of viral genome detection appear to vary since a region of DNA used as a probe or a region amplified by PCR is different in individual studies. Thus, standardized results have not yet been obtained.

In viral myocarditis, the necrosis and slough of cardiac muscle cells of very wide range and a remarkable cellular infiltration of macrophages and NK cells into the cardiac muscle tissue are observed a at the acute phase. It is possible to consider that cellular immunity is induced by viral infection in cardiac muscles. As a result, those cardiac muscle cells infected with a virus are disrupted by NK cells, etc. at the acute phase. Subsequently, at the subacute phase when most of the virus disappears and thereafter, mainly T cells infiltrate. It is considered that these T cells specifically recognize some antigen expressed on cardiac muscle cells and attack cardiac muscle cells, to thereby cause delayed myocardial disorders.

In this case, it has been also shown that tumor necrosis factor (TNF-$\alpha$) acts to worsen myocarditis in an encephalomyocarditis (EMC) viral myocarditis model in mouse (T. Yamada et al., Circulation, 89, 846, 1994). Thus, it is suggested that specific cytokines are also involved in the progress of morbid state.

At present, there is no method established as a specific treatment method for viral myocarditis. However, it has been reported recently that interferon $\alpha$ (IFN-$\alpha$) was effective for a viral myocarditis which appeared to be caused by coxsackievirus B2 and dilated cardiomyopathy-like conditions developed after the myocarditis (A. Heim et al., Clin. Cardiol., 17, 563, 1994). On the other hand, in an experimental mouse model, the effectiveness of ribavirin (an antiviral agent), FK565 (an immune activator), captopril (angiotensin converting enzyme (ACE) inhibitor) and the like has been shown in addition to IFN-$\alpha$ (A. Matsumori, Viral Infections of the Heart (ed. J. E. Bamatvala), Edward Armold, London, p. 110, 1993). In actual clinical scenes, however, at present symptomatic treatment using a cardiac or the like is conducted while monitoring the cardiac functions, rather than a positive antiviral therapy, since the identification of virus has not been established.

Viral myocarditis is a clinical problem particularly because it is considered that the occurrence of not only myocarditis per se but also delayed myocardial disorders may result in dilated cardiomyopathy (Chuichi Kawai, Journal of Japan Medical Association, Vol. 111, p. 56, 1994).

Viral myocarditis often leaves cardiac abnormalities. In other words, about 43% of viral myocarditis patients who have overcome the acute phase are completely cured, but about 40% of them have sequelae and 3.2% of them suffer from recurrence or exacerbation (Keishiro Kawamura et al., 1982 Study Report by the Survey Group on the Specifically Designated Disease by Ministry of Health and Welfare—Idiopathic Cardiomyopathy, p. 16, 1983). Furthermore, in a subsequent trace survey, it has been made clear that a part of those who had had sequelae presented a dilated cardiomyopathy-like morbid picture. Thus, even after the acute phase, a trace for a long term is considered necessary.

Dilated cardiomyopathy is a disease in which the cardiac muscle undergoes a primary degeneration or functional disorders to thereby develop contraction failure and the ventricles are expanded to thereby present the conditions of congestive heart failure. The prognosis of this disease is quite bad. The survival ratios of 5 years and 10 years after the occurrence are 54% and 36%, respectively (Chuichi Kawai et al., 1982 Study Report by the Survey Group on the Specifically Designated Disease by Ministry of Health and Welfare—Idiopathic Cardiomyopathy, p. 63, 1983). For this reason, dilated cardiomyopathy has become one of the most preferential diseases for the application of heart transplantation in Europe and the United States. In Japan, toward the elucidation of its cause and the establishment of its treatment method, dilated cardiomyopathy has become the specifically designated disease by the Ministry of Health and Welfare and a study group has been organized.

Treatment for dilated cardiomyopathy is mainly symptomatic treatment using a digitalis formulation, diuretic, $\beta$ blocker, ACE inhibitor or the like. Although these internal treatment may be effective when the reserve force still remains in the cardiac muscle of a patient, the cardiac muscle reaches its limit through repetition of heart failures. Finally, heart transplantation is necessary for such a patient. With respect to hypertrophic cardiomyopathy, a part of this disease is considered due to myosin heavy chain genetic abnormality, but the cause is unknown for the most part of it. Shift from viral infection cannot be ignored as a cause. A method for treating this disease also has not been established yet.

As described above, a treatment method with high specificity has not yet been established for viral myocarditis as well as dilated cardiomyopathy and hypertrophic cardiomyopathy which develop in association with the myocarditis.

The development of such a treatment method is urgently required. In particular, dilated cardiomyopathy appears to be an "incurable disease" in the present situation. Thus, it is extremely significant to develop a therapeutic agent and a testing method for this disease.

DISCLOSURE OF THE INVENTION

In order to solve the assignments described above, the present invention provides a therapeutic agent for viral myocarditis and other cardiac diseases associated therewith and a method for testing these diseases.

The present invention includes the following inventions.
(1) A therapeutic agent for a cardiac disease in which the cardiac muscle tissue is infected with human hepatitis C virus (hereinafter abbreviated as "HCV"), comprising an antiviral agent as an active ingredient.
(2) The therapeutic agent described in (1) above, wherein the antiviral agent inhibits the growth of human hepatitis C virus.
(3) The therapeutic agent described in (1) above, wherein the antiviral agent is human interferon $\alpha$, $\beta$ or $\gamma$.
(4) The therapeutic agent described in (1) above, wherein the cardiac disease is myocarditis or cardiomyopathy.
(5) The therapeutic agent described in (4) above, wherein the cardiomyopathy is dilated cardiomyopathy or hypertrophic cardiomyopathy.
(6) A method for testing myocarditis or cardiomyopathy by detecting human hepatitis C virus.
(7) Use of an antiviral agent as a therapeutic agent for a cardiac disease in which the cardiac muscle tissue is infected with human hepatitis C virus.
(8) A method for treating a cardiac disease, comprising administering an antiviral agent to a patient having a cardiac disease in which the cardiac muscle tissue is infected with human hepatitis C virus.
(9) A method for treating a cardiac disease, comprising administering an antiviral agent to a patient having myocarditis or cardiomyopathy in which human hepatitis C virus has been detected.

The target cardiac diseases of the invention are viral myocarditis and cardiac diseases associated therewith, i.e., viral myocarditis and those cardiomyopathies in which the participation of virus is recognized. Also, those dilated cardiomyopathy and hypertrophic cardiomyopathy which are possibly related to viral myocarditis are included in the target cardiac diseases of the invention, even though being idiopathic cardiomyopathy of which the cause is unknown.

As already described, in viral myocarditis and dilated cardiomyopathy which can be said the ultimate picture of delayed myocardial disorders developed from viral myocarditis, though enterovirus such as coxsackievirus is considered as one of the causative viruses, participation of various viruses are also suggested. In idiopathic cardiac diseases where participation of such viruses are presumed, the identification of the causative virus is essential for the establishment of an accurate treatment method.

The present inventors have made extensive and intensive researches on the assumption that HCV can participate in cardiac diseases though it has never been reported as a causative virus thereof. As a result, it has become clear that HCV can be a cause for cardiomyopathy. Furthermore, the present inventors have proposed a new treatment method in view of that an antiviral agent inhibiting the growth of HCV, such as interferon (IFN), will be effective for the treatment of idiopathic cardiac diseases in which virus is participating. Thus, the present invention has been achieved.

The diagnosis of viral myocarditis is conducted based on cardiac symptoms (pectoralgia, dyspnea, palpitation, etc.), cold-like symptoms (fever, headache, cough, etc.), symptoms in digestive organs (nausea, vomiting, bellyache, etc.) and tachycardia or bradycardia, or abnormalities found in electrocardiogram. Furthermore, the diagnosis is conducted by identifying HCV serologically or by means of histological test of a cardiac biopsy specimen. The above-mentioned specific items for diagnosis are described in more detail in, for example, the 1988 Study Report and the 1990 Study Report made by the Study Group for the Specifically Designated Disease by Ministry of Health and Welfare—Idiopathic Cardiomyopathy.

Since the identification of HCV is essential in the present invention, a method of using HCV detection techniques for the purpose of diagnosis of viral myocarditis is also included in the present invention. The term "HCV detection techniques" used herein refers to the identification of HCV by bioassay, radioimunoassay, enzyme immunoassay, immunoagglutination, fluorescent antibody technique, electrophoresis, detection of HCV bioactivity, or the like using blood, serum or cardiac muscle biopsy specimen as a sample. From the viewpoint of simplicity and rapidity, serological diagnosis using an anti-HCV antibody or genetic analysis using the RT (reverse transcriptase)-PCR method is preferable. However, considering that the amount of virus in a cardiac muscle biopsy specimen is not necessarily at a detectable level and that the burden of testing on patients should be reduced, actually, the detection of an anti-HCV antibody in a serum is sufficient as the proof of HCV infection.

On the other hand, the diagnosis of dilated cardiomyopathy is conducted based on heart failure, arrhythmia, abnormalities in cardiac sound, abnormalities in electrocardiogram, abnormalities in chest radiograph, abnormalities in cardiac echo, and the like. More specific items for diagnosis are described in, for example, the 1985 Study Report made by the Study Group for the Specifically Designated Disease by Ministry of Health and Welfare—Idiopathic Cardiomyopathy.

The agent used in the invention which reveals inhibiting action against HCV is not particularly limited; any agent may be used as long as it can be used as an antiviral agent. Preferably, human IFN is used. Specific examples of antiviral agents include not only such agents as ribavirin and nucleic acid derivatives that have HCV inhibiting action by themselves, but also agents having IFN inducing action, such as glycyrrhizin formulations, organic germanium compounds, imidazole derivatives and SHO-SAIKO-TO (a Kampo Formula).

The IFN used in the invention may be of any type: $\alpha$-type, $\beta$-type, $\gamma$-type, consensus-type or hybrid-type. In terms of origin, it may be of any of natural-type, recombinant-type or chemically synthesized type. Preferably, IFN-$\alpha$ and IFN-$\beta$ which definitely reveal HCV inhibiting effect are used. Among all, natural-type IFN-$\beta$ is especially preferable. With respect to natural-type interferons, blood system cells and established cell lines thereof are preferably used for the production of $\alpha$-type and $\beta$-type, and fibroblast and established cell lines thereof are preferably used for the production of $\beta$-type.

When an IFN is prepared by using recombinant DNA technology, mammalian cells such as CHO (Chinese hamster ovary) cells, mouse C127 cells, BHK (baby hamster kidney) cells; insect cells such as silkworm and cabbage armyworm; and microorganisms such as *E. coli, Bacillus subtilis* and yeast may be used as a host cell. Further, mouse, rat, hamster, rabbit, goat, sheep, pig, bovine and the like may be used as a transgenic animal.

The thus prepared IFN may be purified and separated from the raw material such as cell culture supernatant, insect extract, microorganism extract, bioextract, blood or milk by various kinds of chromatography. Any chromatography may be used as long as it has affinity with IFN. For example, a column packed with silicon dioxide (silica) or calcium phosphate as an adsorptive material; a column having heparin, a pigment or a hydrophobic group as a ligand; a metal chelate column; an ion exchange column; a gel filtration column and the like may be used.

As the IFN in the present invention, natural-type IFN-β is especially preferable. This natural-type IFN-β can be prepared by the following procedures.

Briefly, IFN-β producing cells cultured on the surface of glass or plastic or on the surface of a microcarrier such as agarose, cuticle or DEAE-dextran are subjected to an induction treatment using, for example, a synthetic double-stranded RNA such as PolyI:C and a subsequent ultrainduction treatment (for example, a metabolism inhibition method using a combination of cycloheximide and actinomycin D or a UV irradiation method). Thereafter, the cells are cultured for additional 24–72 hours in a culture solution, and then a product solution containing human IFN-β produced therein is obtained.

Generally, the thus obtained IFN-β is present at a low concentration in the product solution. Besides, the product solution contains a number of contaminants from the cells or additives in addition to the IFN-β. Therefore, it is necessary to concentrate and purify the IFN-β further for using it for medical purposes.

The method for concentrating and purifying IFN-β is not particularly limited. Preferable is a chromatographic method using a carrier which is obtained by insolubilizing a ligand having affinity with IFN-β (e.g., a blue pigment-bound insoluble carrier and a metal chelate group-bound carrier). Briefly, a material containing crude IFN-β is treated with a blue pigment-bound insoluble carrier. Then, the IFN-β is recovered as a solution using an eluent. Subsequently, the resultant IFN-β solution is treated with a carrier bound to a chelate group obtained by chelating a metal such as zinc. Then, the IFN-β is recovered using an eluent to obtain concentrated and purified IFN-β.

The thus obtained concentrated and purified IFN-β standard product may be formulated into a parenteral or oral formulation and used as a therapeutic agent for cardiac diseases.

As dosage forms for parenteral administration, for example, eye drops, ointments, injections, patches, paints, suppositories, pernasal absorbents, perpulmonary inhalants, percutaneous absorbents, and the like may be enumerated. Liquid formulations may be prepared by conventional methods. For example, usually, IFN may be formulated into an aqueous solution or a suspension, or IFN may be emulsified and embedded in liposome. Solid formulations may be prepared by conventional methods. For example, mannitol, trehalose, sorbitol, lactose, glucose or the like is added to IFN as an excipient and the resultant mixture may be prepared as a lyophilized formulation. Further, this may be powdered. Gelatinized formulation may be prepared by conventional methods. For example, they may be prepared in a state in which IFN is dissolved in a thickener or polysaccharide, such as glycerol, polyethylene glycol, methylcellulose, carboxymethylcellulose, hyaluronic acid, chondroitin sulfate and the like.

As dosage forms for oral administration, IFN may be formulated into an aqueous solution, a suspension and capsules. Further, IFN may be formulated into tablets using sugar, starch, cellulose, a silicate or the like as an excipient.

In any of the formulations, human serum albumin, human immunoglobulin, $\alpha_2$ macroglobulin, amino acids, polysaccharides and the like may be added thereto as a stabilizer. Also, an alcohol, sugar alcohol, ionic surfactant, non-ionic surfactant or the like may be added as a dispersant or an absorption promoter within a range of amount which will not damage the physiological activity of IFN. Trace metals or salts of organic acid may also be added, if necessary.

The amount of administration of the therapeutic agent of the invention for cardiac diseases is decided appropriately depending on the age, weight, disease to be treated and conditions of a patient and the dosage form and administration route of the agent, and so forth. When IFN-β is used as an antiviral agent (an active ingredient) which inhibits the growth of human hepatitis C virus, generally, 10,000 IU–10,000,000 IU/day, preferably 1,000,000 IU–6,000,000 IU/day are administered as IFN-β for a period which can achieve a treatment effect.

BEST MODES FOR CARRYING OUT THE INVENTION

Hereinbelow, the present invention will be described in more detail with reference to the following Examples. However, the present invention is not limited to these Examples.

EXAMPLE 1

Identification of Virus in Patients with Cardiac Diseases

In order to clarify the participation of virus in cardiac diseases, a serological test on cardiac disease patients and the identification of virus in their cardiac muscle specimens by the RT-PCR method were conducted. The subjects of these experiments were 40 cases of ischemic cardiac diseases (male: 24 cases; female: 16 cases; average age: 57.7±8.2) and 36 cases of dilated cardiomyopathy (male: 25 cases; female: 11 cases; average age: 46.5±15.8).

For the detection of anti-HCV antibodies, blood was taken from patients. Then, sera were separated immediately and stored at −80° C. until the time of testing. For the detection, the second generation radioimmunoassay of Ortho Diagnostics (Ranton, N.J., USA) was used. HCV-RNA in sera was determined according to a previously described method (H. Hagiwara et al., Hepatalogy, 17, 545, 1993).

After the acquisition of an informed consent from each patient, cardiac muscle specimens were taken from the internal wall of the right ventricle when a cardiac catheter was inserted using cardiac muscle biopsy forceps. Five samples were taken from each site, and two of them were immediately placed in liquid nitrogen and stored there until use as samples for testing virus. At the time of testing, a frozen sample was dissolved in 200 µl of a solution containing 4 M guanidine thiocyanate/25 mM citric acid (pH 7.0)/5% sarcosyl/0.1 M mercaptoethanol and RNA was extracted according to a previously described method (T- L. Fong et al., J. Clin. Invest., 88, 1058, 1991).

PCR was performed with Taq polymerase after single-stranded cDNA's were synthesized using murine leukemia reverse transcriptase. Amplification reaction was carried out as follows: one cycle of at 92° C. for 5 minutes, at 55° C. for 2 minutes and at 72° C. for 3 minutes, and then 35 cycles of at 95° C. for 1 minute, at 55° C. for 1 minute and at 72° C. for 2 minutes. The secondary amplification was similarly carried out with 35 cycles. As primers, four 20- to 25-mers from the well-preserved 5'-noncoding region of HCV (sense nucleotides Nos. 29–53 and Nos. 54–73, antisense nucleotides Nos. 310–334 and Nos. 179–198) were used. PCR products were detected by electrophoresis using 3% agarose gel containing ethidium bromide (1 μg/ml).

The results of the detection of anti-HCV antibodies in sera are as shown in Table 1. Briefly, 16.7% of the patients diagnosed as having dilated cardiomyopathy are positive for anti-HCV antibodies in sera. Statistically, this ratio is significantly ($p<0.05$) higher than the positive ratio of 2.5% in the patients having an ischemic cardiac disease. Thus, the relation between dilated cardiomyopathy and HCV has been strongly suggested.

TABLE 1

Appearance Ratio of Anti-HCV Antibody in Sera of Cardiac Disease Patients

| Disease | Number of Cases (Male/Female) | Anti-HCV Antibody Positive | Positive Ratio |
|---|---|---|---|
| Dilated cardiomyopathy | 36 (25/11) | 6 | 16.7% |
| Ischernic cardiac diseases | 40 (24/16) | 1 | 2.5% |

*Significance test by Fisher's direct probability calculation method ($p = 0.039$)

Further, in the 6 cases of dilated cardiomyopathy which were anti-HCV antibody positive, the detection of HCV-RNA in cardiac muscle specimens was conducted by the RT-PCR method. The results are as shown in Table 2.

TABLE 2

Detection of HCV-RNA in Cardiac Muscle Specimens from Dilated Cardiomyopathy Patients

| Analysis Items | Case | | | | | |
|---|---|---|---|---|---|---|
|  | 1 | 2 | 3 | 4 | 5 | 6 |
| Age | 57 | 22 | 61 | 66 | 51 | 17 |
| Sex | female | male | male | female | female | female |

TABLE 2-continued

Detection of HCV-RNA in Cardiac Muscle Specimens from Dilated Cardiomyopathy Patients

| Analysis Items | Case | | | | | |
|---|---|---|---|---|---|---|
|  | 1 | 2 | 3 | 4 | 5 | 6 |
| Anti-HCV antibody in serum | + | + | + | + | + | + |
| HCV-RNA in serum | + | + | − | + | + | − |
| HCV type | II | II | − | II | II | − |
| HCV-RNA positive strand in cardiac muscle | + | + | − | ND | + | − |
| HCV-RNA negative strand in cardiac muscle | + | − | ND | ND | − | − |

ND: not tested.

As shown in Table 2, HCV-RNA is detected in cardiac muscle specimens in at least 3 cases out of the 6 cases tested, and it was found that their cardiac muscles were infected with HCV even at the time of testing. PCR products at this time were about 145 bp and found to be of genome type II. Those cases which are HCV-RNA negative in cardiac muscle specimens and positive for anti-HCV antibody in sera are presumed to have been infected with HCV in the past.

On the other hand, a serological test and a cardiac muscle biopsy were conducted on 35 patients with hypertrophic cardiomyopathy (male: 25; female: 10; average age: 55.8±11.6). As a result, it was found that 6 patients out of the 35 patients (17.1%) are anti-HCV antibody positive. This frequency is significantly higher than the frequency in the total patients with ischemic cardiac disease (2.5%) ($p<0.05$). The results of HCV-related tests on these 6 anti-HCV antibody positive patients are as shown in Table 3.

TABLE 3

Detection of HCV-RNA in Cardiac Muscle Specimens from Hypertrophic Cardiomyopathy Patients

| Analysis Items | Case | | | | | |
|---|---|---|---|---|---|---|
|  | 1 | 2 | 3 | 4 | 5 | 6 |
| Age | 64 | 56 | 50 | 56 | 65 | 60 |
| Sex | male | male | female | male | female | female |
| Symptoms | Dyspnea | Ventricular tachycardia | Ventricular tachycardia | Ventricular fibrillation | Dyspnea | No symptoms |
| AST (11-27 IU/L)* | 50 | 43 | 19 | 31 | 24 | 27 |
| ALT (6-27 IU/L)* | 50 | 20 | 29 | 26 | 18 | 17 |
| Anti-HCV antibody in serum | + | + | + | + | + | + |
| HCV-RNA in serum | − | − | + | + | − | − |
| HCV type | − | − | II | II | − | − |
| HCV titer | − | − | $4 \times 10^6$ | $8 \times 10^4$ | − | − |
| HCV-RNA positive strand in cardiac muscle | + | + | + | ND | − | ND |

AST: aspartate aminotransferase
ALT: alanine aminotransferase
*: normal value
ND: not tested As shown in Table 3, HCV-RNA is detected in cardiac muscle specimens in at least 3 cases out of the 6 cases tested, and it was found that their cardiac muscles were infected with HCV even at the time of testing and that patients with hypertrophic cardiomyopathy are infected with HCV in the cardiac muscle at a high ratio.

From the results so far described, anti-HCV antibodies are detected in dilated cardiomyopathy patients and hypertrophic cardiomyopathy patients at significantly higher ratios, and HCV-RNA is detected in cardiac muscle specimens in at least half of those cases. From these facts, the participation of HCV in the development of dilated cardiomyopathy is strongly suggested.

Separate from the subject examination, in order to search for viruses infecting cardiac muscles, PCR was conducted on 36 cases of myocarditis and cardiomyopathy for RNA viruses such as enterovirus, cardiovirus, hepatitis A virus, human immunodeficiency virus (type 1 and type 2), T cell leukemia virus, influenza virus (A and B) and reovirus; and on 25 cases for DNA viruses such as adenovirus, cytomegalovirus, EB virus, hepatitis B virus, herpesvirus 6, varicella zoster virus and herpes simplex virus (1 and 2). However, with respect to the group of these viruses, only enterovirus RNA was detected in one case (detection ratio: 2.8%). This ratio is significantly low than the detection ratio of HCV (3/36=8.3%), suggesting that the participation of HCV is greater than that of enterovirus.

EXAMPLE 2

Effect of IFN on Mouse EMC Viral Myocarditis (1)

EMC virus (10 pfu/0.1 ml) was inoculated into the abdominal cavity of 3 groups of 4-week old, male DBA/2 mice, each group consisting of 12 mice. The control group received 0.1 ml of physiological saline only. For Group A, $10^5$ IU/0.1 ml of E. coli recombinant-type mouse IFN-β (Toray Industries) was administered into the abdominal cavity one day before the EMC virus inoculation. For Group B, $10^5$ IU/0.1 ml of mouse IFN-β was administered into the abdominal cavity simultaneously with the virus inoculation. Four days after the virus inoculation, 6 mice in each group were slaughtered and the amount of EMC virus in the cardiac muscle was quantitatively determined. Seven days after the virus inoculation, 6 mice in each group were slaughtered, and cellular infiltration pictures, necrosis foci and the like resulted from the inflammation of the cardiac muscle were examined histologically. Both tests were conducted in accordance with a previously described method (A. Matsumori et al., J. Am. Coll. Cardiol., 9, 1320, 1987).

As seen from the results shown in Table 4, the growth of EMC virus and cardiac muscle lesions are remarkably reduced by the administration of IFN-β. The EMC virus-infected DBA/2 mouse model used here has been shown to progress, after the development of viral myocarditis, into hypertrophy of the heart, cardiac dilatation and the like at the chronic phase which resemble the morbid pictures of dilated cardiomyopathy (A. Matsumori and C. Kawai, Circulation, 65, 1230, 1982). From this, it has been shown that the shift from viral myocarditis to dilated cardiomyopathy can be blocked by the administration of IFN-β.

TABLE 4

Effect of IFN on Mouse EMC Viral Myocarditis (1)

| Experimental Group | Viral Titer in Cardiac Muscle (log pfu/mg) | Extent of Cellular Infiltration (Grade 0–4)[1] | Extent of Necrosis Foci Grade 0–4)[1] |
|---|---|---|---|
| Control group | 4.5 ± 0.5 | 3.5 ± 0.7 | 3.8 ± 0.5 |
| Group A | 3.0 ± 0.2* | 0.2 ± 0.3** | 0.2 ± 0.3** |
| Group B | 3.2 ± 0.4* | 1.0 ± 0.6** | 1.2 ± 0.5** |

*p < 0.05,
**p < 0.01
[1]Grade: "0": Diseased area 0%
"1": 0% < Diseased area ≦ 25%
"2": 25% < Diseased area ≦ 50%
"3": 50% < Diseased area ≦ 75%
"4": 75% < Diseased area ≦ 100%

EXAMPLE 3

Effect of IFN on Mouse EMC Viral Myocarditis (2)

EMC virus (10 pfu/0.1 ml) was inoculated into the abdominal cavity of 4 groups of 4-week old, male DBA/2 mice. The control group received 0.1 ml of phosphate-buffered physiological saline (PBS) only. For IFN administration groups, $10^4$ IU/0.1 ml (Group C) or $10^5$ IU/0.1 ml (Group D) of E. coli recombinant-type mouse IFN-β (Toray Industries) was administered subcutaneously on the day of the virus inoculation, and one day, 2 days and 3 days after the inoculation. Seven days after the inoculation, the number of survival was examined.

The weight of the heart in survived mice was measured, and the cellular infiltration and necrosis foci in the cardiac muscle reflecting myocarditis were examined as described in Example 2.

As seen from the results shown in Table 5, the mortality of mice is significantly decreased by the administration of IFN-β, In the survived mice, it has been found that hypertrophy of the heart and cardiac muscle lesions are inhibited and that their hearts remain close to the normal level (i.e., the level of EMC virus non-inoculation group). From these results, the treatment effect of IFN-β on viral myocarditis has been demonstrated.

TABLE 5

Effect of IFN on Mouse EMC Viral Myocarditis (2)

| Experimental Group | No. of Survived Mice/ No. of Treated Mice (%: Survival Ratio) | Heart Weight (mg)/ Body Weight (g) | Extent of Cellular Infiltration (Grade 0–4)[1] | Extent of Necrosis Foci (Grade 0–4)[1] |
|---|---|---|---|---|
| EMC Virus Inoculation Groups | | | | |
| Control group (PBS) | 5/10 (50%) | 9.0 ± 0.4 | 2.6 ± 0.4 | 2.4 ± 0.2 |

TABLE 5-continued

Effect of IFN on Mouse EMC Viral Myocarditis (2)

| Experimental Group | No. of Survived Mice/ No. of Treated Mice (%: Survival Ratio) | Heart Weight (mg)/ Body Weight (g) | Extent of Cellular Infiltration (Grade 0–4)[1] | Extent of Necrosis Foci (Grade 0–4)[1] |
|---|---|---|---|---|
| Group C (IFN, $10^4$ IU) | 9/10 (90%) | 7.3 ± 0.6 | 1.9 ± 0.5 | 1.9 ± 0.5 |
| Group D (IFN, $10^5$ IU) | 10/10* (100%) | 5.2 ± 0.3*** | 0.5 ± 0.3** | 0.5 ± 0.3** |
| EMC Virus Non-inoculation Group | 15/15 (100%) | 4.9 ± 0.1 | 0.0 ± 0.0 | 0.0 ± 0.0 |

*$p < 0.05$, **$p < 0.01$, $p < 0.005$
[1] Grade: "0": Diseased area 0%
"1": 0% < Diseased area ≤ 25%
"2": 25% < Diseased area ≤ 50%
"3": 50% < Diseased area ≤ 75%
"4": 75% < Diseased area ≤ 100%

INDUSTRIAL APPLICABILITY

The therapeutic agent of the invention for cardiac diseases is useful as a therapeutic agent for treating viral myocarditis and other cardiac diseases associated therewith.

What is claimed is:

1. A method for testing for human hepatitis C virus in a patient having a myocarditis or a cardiomyopathy comprising taking a cardiac muscle specimen from the patient and detecting human hepatitis C virus in the cardiac muscle specimen.

2. The method of claim 1, wherein the human hepatitis C virus is detected by a means selected from the group consisting of bioassay, radioimmunoassay, enzyme immunoassay, immunoagglutination, fluorescent antibody technique, electrophoresis, detection of bioactivity of human hepatitis C virus, serological diagnosis using an antibody against human hepatitis C virus and genetic analysis using the reverse transcriptase-PCR method.

3. The method of claim 1, wherein the cardiomyopathy is dilated cardiomyopathy or hypertrophic cardiomyopathy.

* * * * *